(12) United States Patent
Steiner et al.

(10) Patent No.: US 8,287,548 B2
(45) Date of Patent: Oct. 16, 2012

(54) WIRE FIXATION DEVICE

(75) Inventors: Christian Steiner, Eisenach (DE);
Meinrad Fiechter, Münsingen (CH);
Beat Knuchel, Ursenbach (CH);
Vinzenz Burgherr, Wabern (CH)

(73) Assignee: Stryker Trauma SA (CH)

( * ) Notice: Subject to any disclaimer, the term of this patent is extended or adjusted under 35 U.S.C. 154(b) by 791 days.

(21) Appl. No.: 12/286,297

(22) Filed: Sep. 29, 2008

(65) Prior Publication Data

US 2009/0198292 A1 Aug. 6, 2009

(30) Foreign Application Priority Data

Feb. 1, 2008 (EP) ..................................... 08150953

(51) Int. Cl.
*A61B 17/58* (2006.01)
(52) U.S. Cl. ............................ 606/96; 606/103; 606/104
(58) Field of Classification Search .................... 606/54, 606/263, 271, 69–98, 102–104, 328–329; 279/57; 24/136 R, 136; 403/290, 297, 298, 403/302–304, 306, 315, 319, 344, 355, 362, 403/371; 248/74.3, 74.4, 74.5, 73, 50
See application file for complete search history.

(56) References Cited

U.S. PATENT DOCUMENTS

| | | | |
|---|---|---|---|
| 3,718,340 A * | 2/1973 | Stewart | 279/57 |
| 5,275,598 A | 1/1994 | Cook | |
| 5,630,814 A | 5/1997 | Ross et al. | |
| 6,827,722 B1 * | 12/2004 | Schoenefeld | 606/104 |
| 7,628,571 B2 * | 12/2009 | Chen | 409/234 |
| 2009/0306661 A1 * | 12/2009 | Thomke et al. | 606/54 |

FOREIGN PATENT DOCUMENTS

| | | |
|---|---|---|
| GB | 2425958 | 11/2006 |
| WO | WO-95/05127 | 2/1995 |
| WO | WO 9505127 A2 * | 2/1995 |

* cited by examiner

*Primary Examiner* — Kevin T Truong
*Assistant Examiner* — Diana S Jones
(74) *Attorney, Agent, or Firm* — Lerner, David, Littenberg, Krumholz & Mentlik, LLP

(57) ABSTRACT

A wire or pin fixation and tensioning device has a wire post having a head portion with an opening having a predetermined longitudinal axis for reception of a wire or pin. The wire post has a neck portion for engaging an opening of the medical device. A locking element is adapted to be introduced into opening having an opening with inclined sections inclined to the longitudinal axis. A clamping cone abuts an abutment element and has a clamping opening to accommodate a wire and has outer surfaces inclined to the longitudinal axis and encompassed within the conical section of the locking element. Upon an axial displacement of the locking element relative to the cone a radial force is exerted onto the cone leading to a reduction of the diameter of the clamping opening to apply a radial force onto a wire or pin therein.

20 Claims, 6 Drawing Sheets

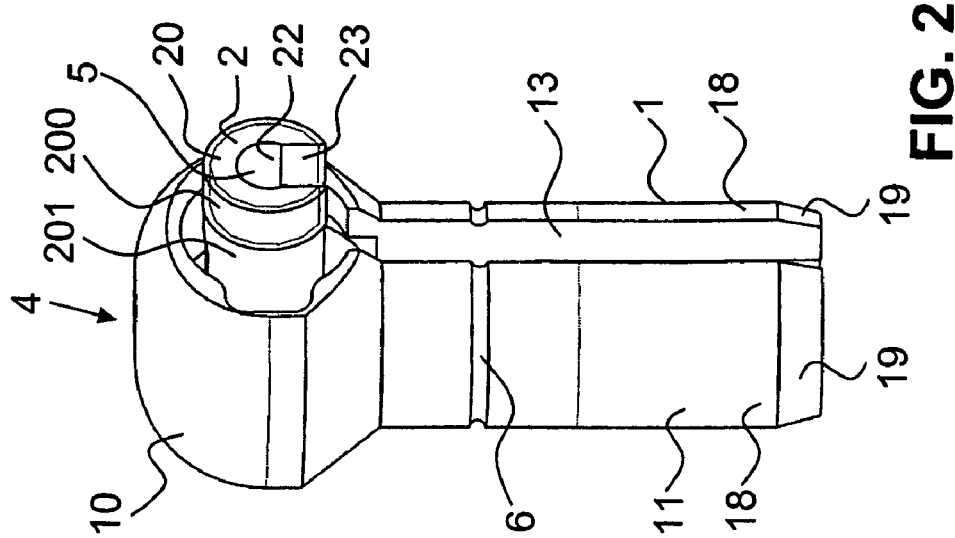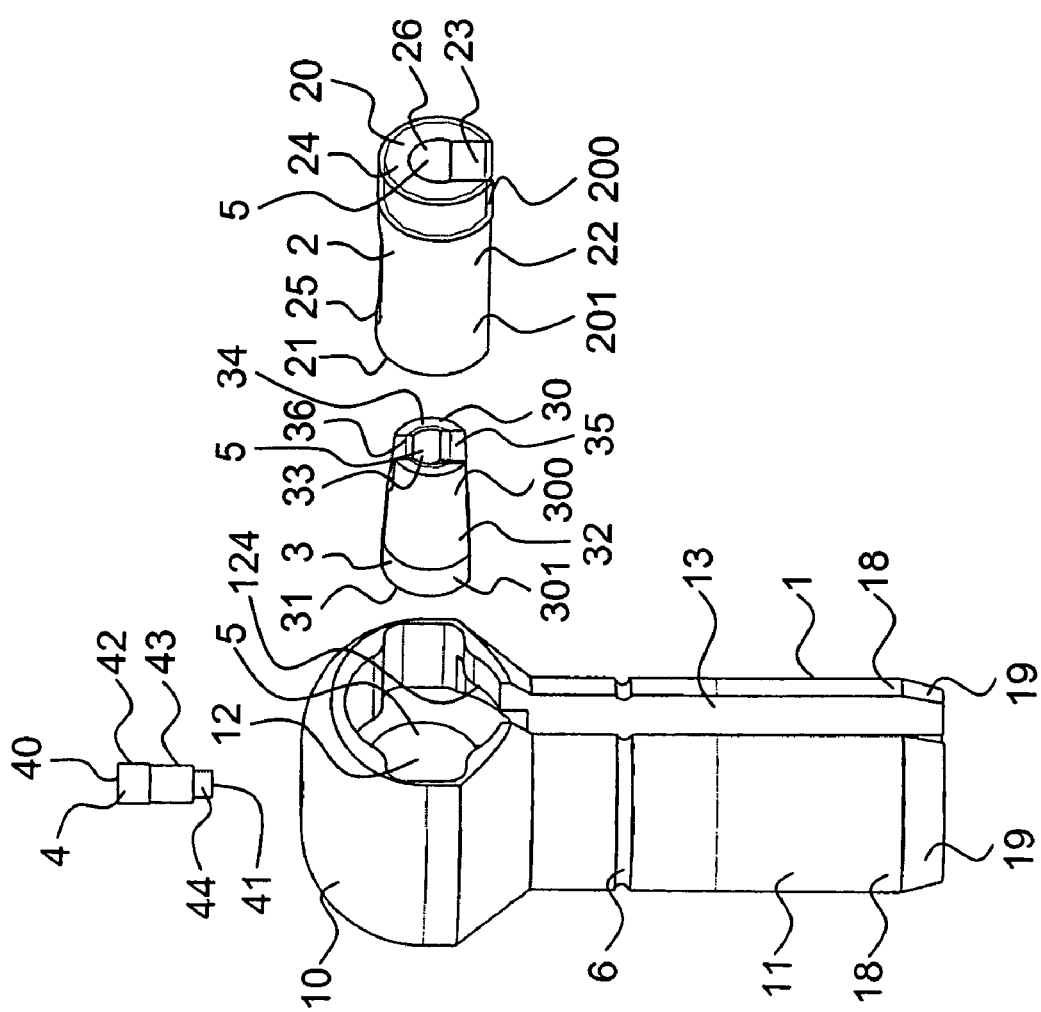

WIRE FIXATION DEVICE

BACKGROUND OF THE INVENTION

The invention relates to a device for connecting a wire for being in connection with a bony structure and with a frame of a medical device.

Prior art teaches several devices to connect a wire that is in connection with a bony structure to a medical device such as a frame of an external fixation system. Such frames can have different shapes, for example the shape of a circle, a segment of a circle, rectangular etc. Said wires are also known as Kirschner-Wires (K-Wire) and are drilled through the bone to hold bone fragments in a fixed position. The K-Wires have to be tensioned with forces up to 1000 Newton or even more depending on the situation. After being tensioned said K-Wire has to be clamped and fixed with the external medical device, such as an external fixation system.

U.S. Pat. No. 5,275,598 for example teaches the use of bolts and nuts to fix wires to a ring of an external fixator. Such a fixation technique requires the use of a K-Wire Tension device which is oriented radial to the ring and other tools such as wrenches to tighten the bolt/nut connection. Other methods of attaching K-Wires are shown in U.S. Pat. Nos. 5,741,252 and 6,342,054.

The use of wrenches leads to complications and is cumbersome for the medical practitioner as it needs much space in axial and radial direction. This limits the operation and handling freedom.

SUMMARY OF THE INVENTION

An object of the present invention is to provide a wire fixation device for connecting and fixing a wire to an external medical device, whereby the device according to the present invention shall overcome the disadvantages of prior art. In particular the maximum space needed for mounting and fixing the wire to the wire fixation device shall be limited.

According to the invention there is provided a wire fixation device for fixing a wire or a pin to a medical device comprising a wire post having a head portion with an opening having a predetermined longitudinal axis for reception of said wire and a neck portion for being in engagement with an opening of the medical device, a locking element adapted to be introduced into the opening having an reception with inclined sections that are inclined to the longitudinal axis, an abutment element, and a clamping cone abutting on said abutment element. The clamping cone having a clamping opening to accommodate a wire and inclined outer surfaces that are inclined to the longitudinal axis and which are encompassed with the conical section of the locking element. Upon an axial displacement of the locking element relative to the clamping cone a radial force is exerted onto the clamping cone leading to a reduction of the diameter of the clamping opening such that if a wire or a pin is inserted into the clamping opening a radial force results onto the wire or the pin.

The wire is preferably tensioned. With such a wire fixation device the medical practitioner is able to fasten a wire within a limited space.

Preferably the inclined section and the inclined outer surface are plane surfaces or curved surfaces. The curved surfaces result preferably in a conical structure. The inclined section may also be designated as inclined surface.

Preferably the neck portion is elongated and substantially cylindrical and comprises a slot extending through the neck portion from an end face being opposite the head portion to the opening of the head portion. The locking element and the clamping cone each comprise a slot extending along axial direction over the whole length of the respective sidewall and along radial direction from the respective circumferential surface into the respective reception or clamping opening.

Preferably the slot in the clamping cone has a width that is smaller than the diameter of the wire.

This is particularly advantageous as the wire can be held in radial direction by means of the clamping opening and is still moveable in axial direction as long as no radial force is exerted onto the wire.

Preferably the locking element and the clamping cone are arranged such with respect to each other and to the wire post that a through slot is being provided in order to introduce the wire via the slot in the wire post, via the slot in the locking element and via the slot in the clamping cone into the clamping opening.

Such an arrangement allows that the wire fixation device is imposed on or slipped over a wire.

Preferably the head portion comprises an opening in which a bolt is introduceable, wherein said bolt engages in a groove that is arranged in the locking element such that the locking element will be held fixed in radial direction and moveable in axial direction.

Preferably the abutment element is provided by means of said bolt and an abutment shoulder, wherein the bolt engages into a longitudinal groove that is arranged in the clamping cone and that comprises an abutment surface and is open towards a first end face and wherein the clamping cone abuts on said abutment shoulder the other end face.

Preferably the abutment element is provided by means of said bolt and an abutment groove, wherein the dimension of said abutment groove is limited in a direction along the longitudinal axis by means of an abutment face such that upon an axial force the bolt abuts on said abutment face.

BRIEF DESCRIPTION OF THE DRAWINGS

The drawings will be explained in greater detail by means of a description of an exemplary embodiment, with reference to the following figures:

FIG. 1 shows a perspective explosion view of an embodiment of a wire fixation device according to the present invention;

FIG. 2 shows a perspective view of an assembled wire fixation device according FIG. 1;

DETAILED DESCRIPTION

Figure 3:
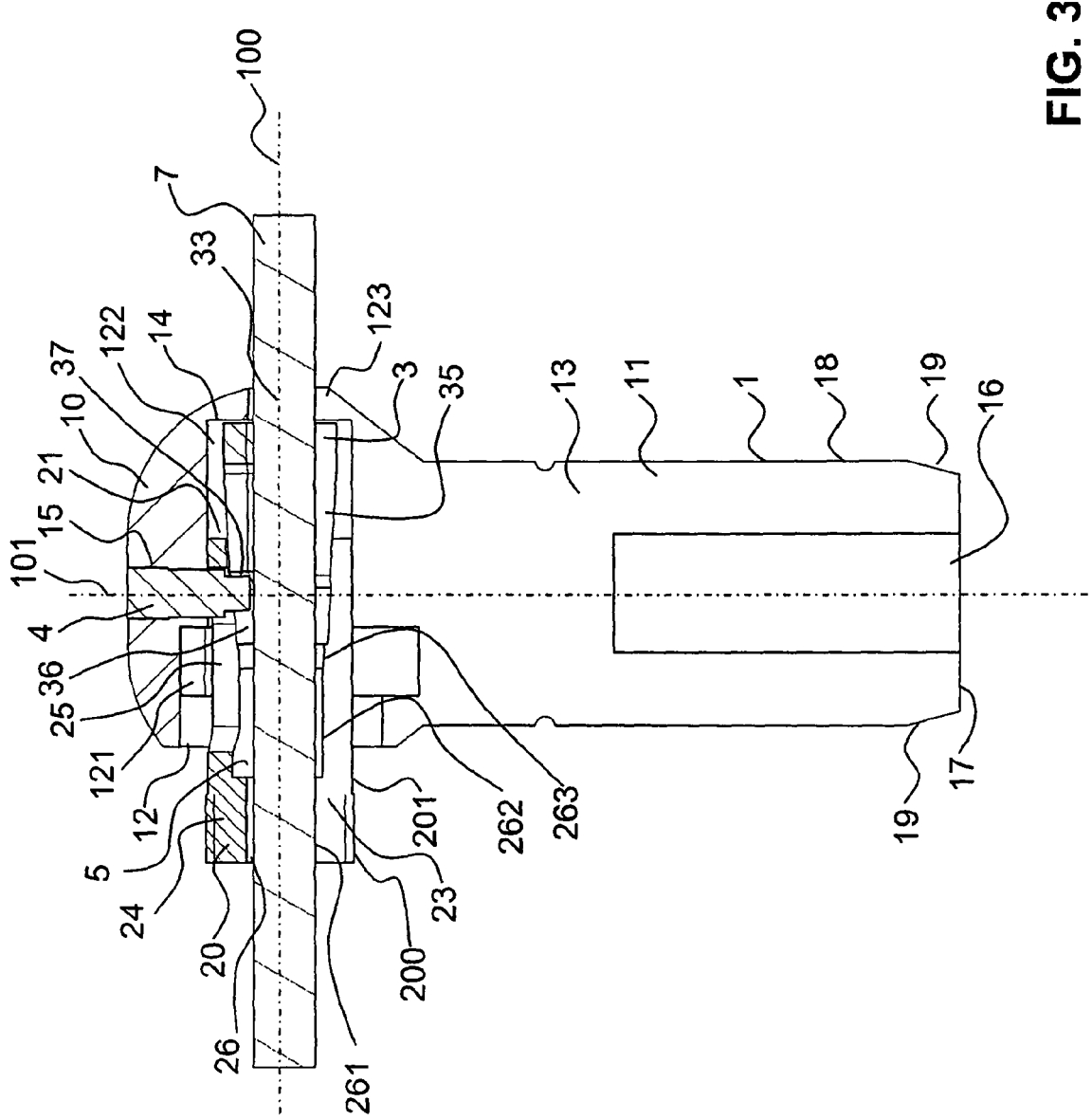
FIG. 3 shows a section view of an assembled wire fixation device according FIG. 1.

FIGS. 1 and 2 show a wire fixation device according to the present invention. The wire fixation device is provided for fixing a tensioned wire (e.g. a Kirscher-Wire) that is an engagement with a bony structure or bone fragments to a medical device such as an external fixator. This means that wire fixation device provides a connection between the wire and the medical device.

The wire fixation device comprises a wire post 1, a locking element 2, a clamping cone 3 and a bolt 4. The wire fixation device comprises further a through opening 5 into which a wire can be inserted. Through opening 5 is preferably provided by the wire post 1, the locking element 2 and the clamping cone 3 as described below. The width or clearance of opening 5 will be influenced due to axial and/or radial displacement and deformation of the wire post 1, the locking element 2 and/or the clamping cone 3 with respect to each other.

The wire post 1 comprises a head portion 10 and a neck portion 11. Said neck portion extends along a longitudinal axis 101 which can be seen in FIG. 3 from the head portion 10. The head portion 10 is adapted to receive elements (i.e. the locking element 2 and the clamping cone 3) being able to hold the wire with respect to the wire fixation device in a fixed manner. The neck portion 11 is provided to be inserted into an opening of an external fixator or to be connected in another manner with an external fixator.

FIG. 3 shows a cross-sectional view of the wire fixation device according to the present invention. The head portion 10 comprises an opening 12 which extends along a middle axis 100 through the head portion 10. Opening 12 forms a part of the opening 5 through which the wire extends once it has been inserted. In the present embodiment the middle axis 100 is angular, here perpendicular to the longitudinal axis 101. However, it has to be noted that any other angle between 15° and 165° can be chosen. This means that the opening 12 defines the direction of the opening 5. The opening 12 comprises preferably a first section 121, a second section 122 and a third section 123.

The first section 121 has a diameter or width that is larger than the diameter of the other two sections 122, 123. The second section 122 is adapted to receive the clamping cone 3 and parts of the locking element 2 and has therefore a cross-sectional shape that corresponds with the outer shape of the locking element 2. The third section 123 comprises a smaller diameter than the second section 122 and provides thereby an abutment shoulder 14 which limits the second section 122. The abutment shoulder 14 functions as stop device for the clamping cone 3. Like the second section 122, the third section 123 is preferably cylindrical. The diameter of the first section is preferably larger than the diameter of the locking element 2 to be inserted into opening 12 via said first section 121.

Figure 6A:
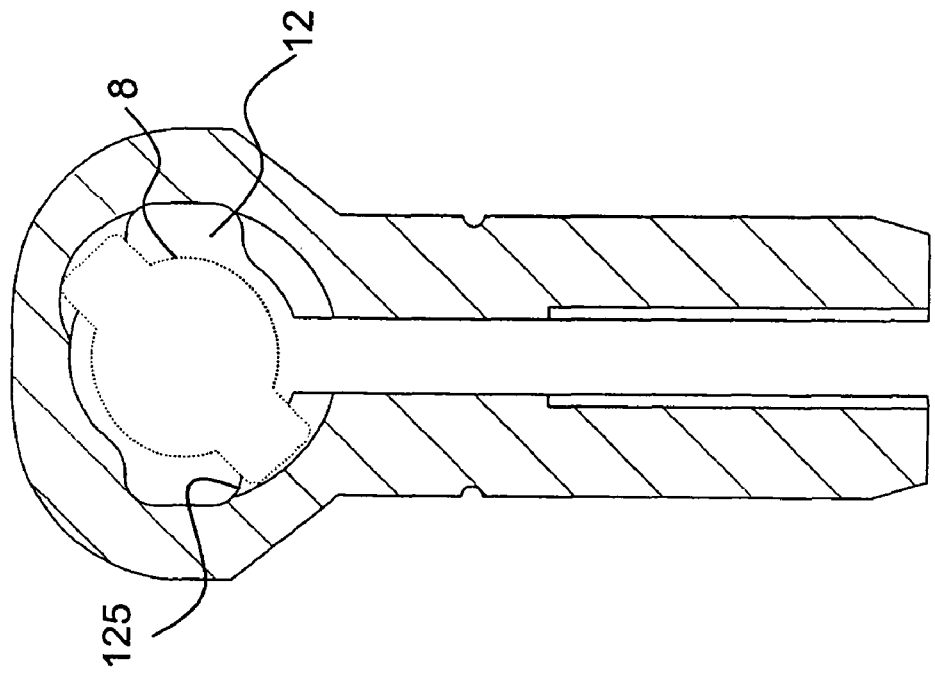
FIGS. 6*a/b* show a front view or a section view, respectively of a wire post of a wire fixation device according FIG. 1.
Figure 6B:
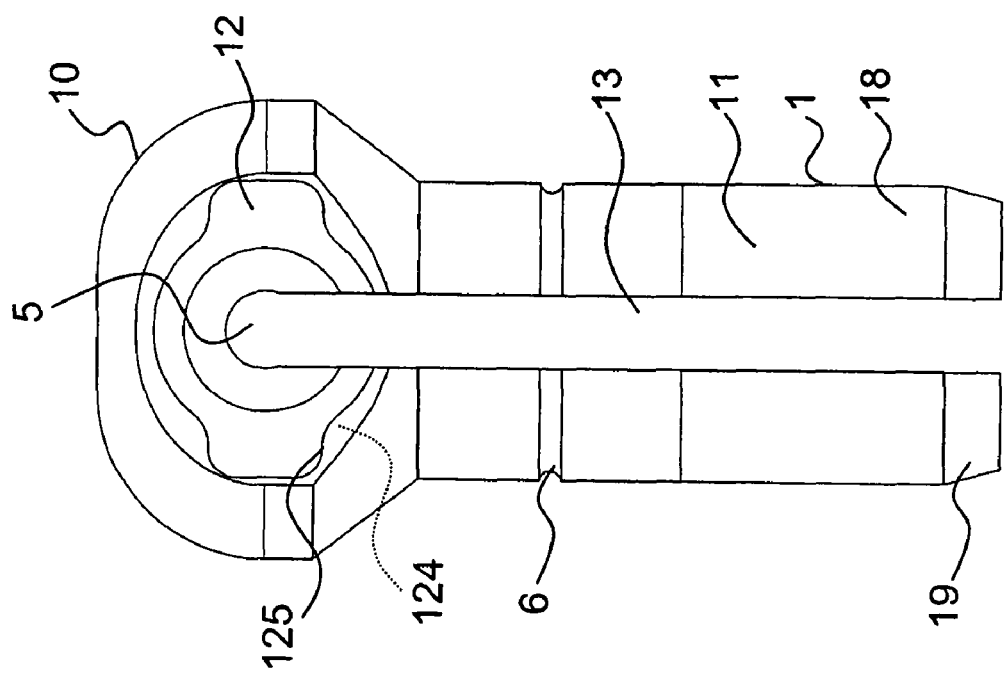

The first section 121 may be designed such that a tool to advance the locking element 2 with respect to the clamping cone 3 and the wire post 1 is engageable with the first section 121. Thereby the tool is engaged in such a manner that it is fixed against axial displacements relative to the wire post 1. Reference is made to FIG. 1 and 6a/b in which it is visible that the first section 121 comprises a groove 124 and a shoulder 125. The groove 124 is thereby arranged behind shoulder 125 as viewed in axial direction such that the groove 124 provides a reception for said tool. Thereby a tool with a flange is inserted through the opening 12 until the flange reaches the groove 124. Afterwards the tool will be rotated around its own axis such that a flange is in an engagement with the groove 124. Due to the engagement the tool is fixed to the wire post in axial direction. FIG. 6b shows a section view through said groove 124. The shape of a schematic tool 8 in the groove 124 is shown in broken lines in FIG. 6a.

Figure 5:
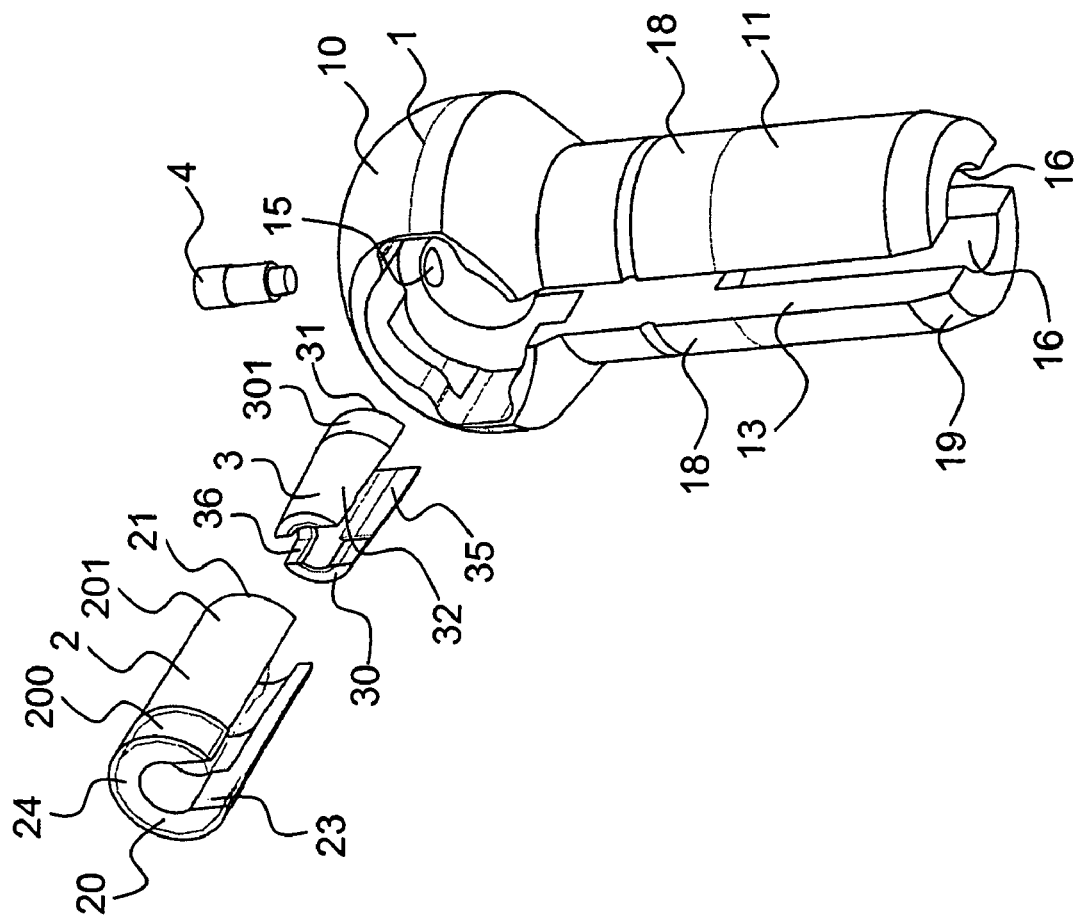
FIG. 5 shows a perspective explosion view of FIG. 4.
Figure 4:
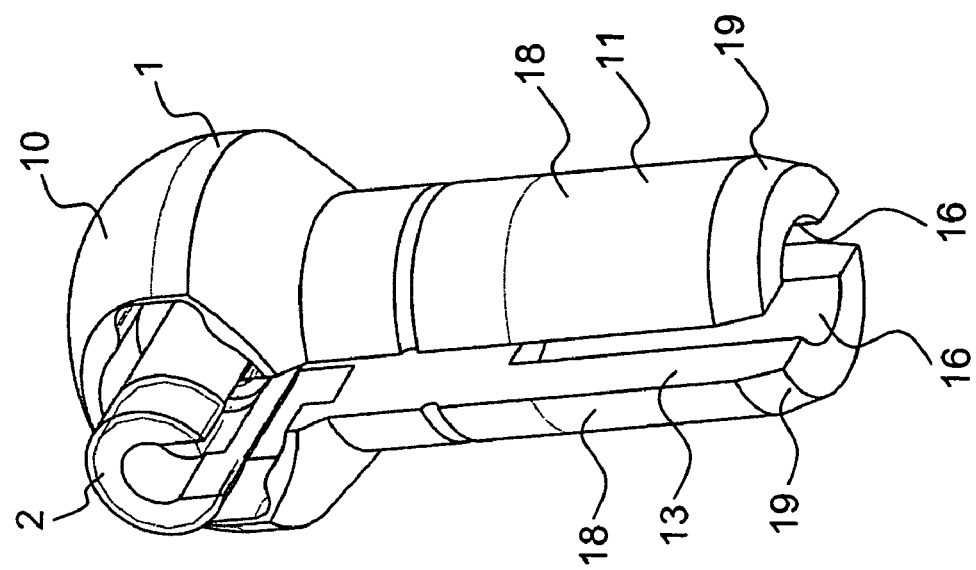
FIG. 4 shows a perspective view from below of an assembled wire fixation device according FIG. 1.

As shown in FIG. 5 the head portion further comprises a bolt opening 15. Bolt opening 15 is arranged angular to the opening 12 and extends through the head portion 10 into the latter. Preferably bolt opening 15 extends along axis 101. Bolt opening 15 is provided to accommodate the bolt 4.

The neck portion 11 comprises a slot 13 extending through the neck portion 11 from an end face 17 into the head portion 10 such that it extends into the opening 12 or opening 5, respectively. The end face 17 is thereby the face that is on the opposite side of the head portion along axis 101. Due to the slot 13 the wire post 1 can be imposed on or slipped over a wire, wherein the wire passes the slot 13 first, before it reaches the opening 12; 5. The outer surface of the neck portion 11 is substantially cylindrical such that it can be introduced into a cylindrical opening of a medical device such as an external fixator. With other words the slot 13 is arranged such that the neck portion 11 comprises two legs 18 extending from the head portion along a longitudinal axis 101, wherein said legs 18 are separated by the slot 13. It has to be noted however, that the neck portion 11 may also have a rectangular, quadratic, elliptical, triangular or polygonal cross section, wherein said cross section depends on the shape of the opening of the medical device.

Additionally legs 18 may comprise recesses 16 extending into the legs from the end face 17 and on the surface that is directed to the slot 13. Recesses 16 have preferably the shape of a segment of a circle. Once the wire post 1 has been introduced into the opening of a medical device, a bolt (not shown) can be introduced into the slot 13 such that it is in an engagement with the recesses 16. Thereby a force radial to axis 101 is provided onto the opening, wherein the connection between the wire fixation device and the medical device can be secured. It has to be noted however, that fixation is purely optional and that the wire fixation device can also be arranged within an opening without the bolt. If used without the locking bolt, the external force from the tensioned wire jams the wire post within the ring hole. Preferably the outer surface of the two legs 18 is provided with an adequate roughness or relief or friction increasing coating in order to support the locking within the ring hole.

Legs 18 further comprises a beveled edge 19 in order to simplify the inserting procedure of the wire post into the opening of a medical device. Beveled edge 19 is arranged at the intersection of the end face 17 and the outer surface of the cylindrical force.

The neck portion 11 comprises furthermore a groove or marking 6 which is arranged on the surface of the neck portion. Marking 6 gives an indication to the medical practitioner concerning the introduction of the neck portion 11 into a corresponding opening in a medical device. The neck portion 11 has to be introduced such that the marking 6 is either flush with the beginning of the opening or within the opening.

Figure 8:
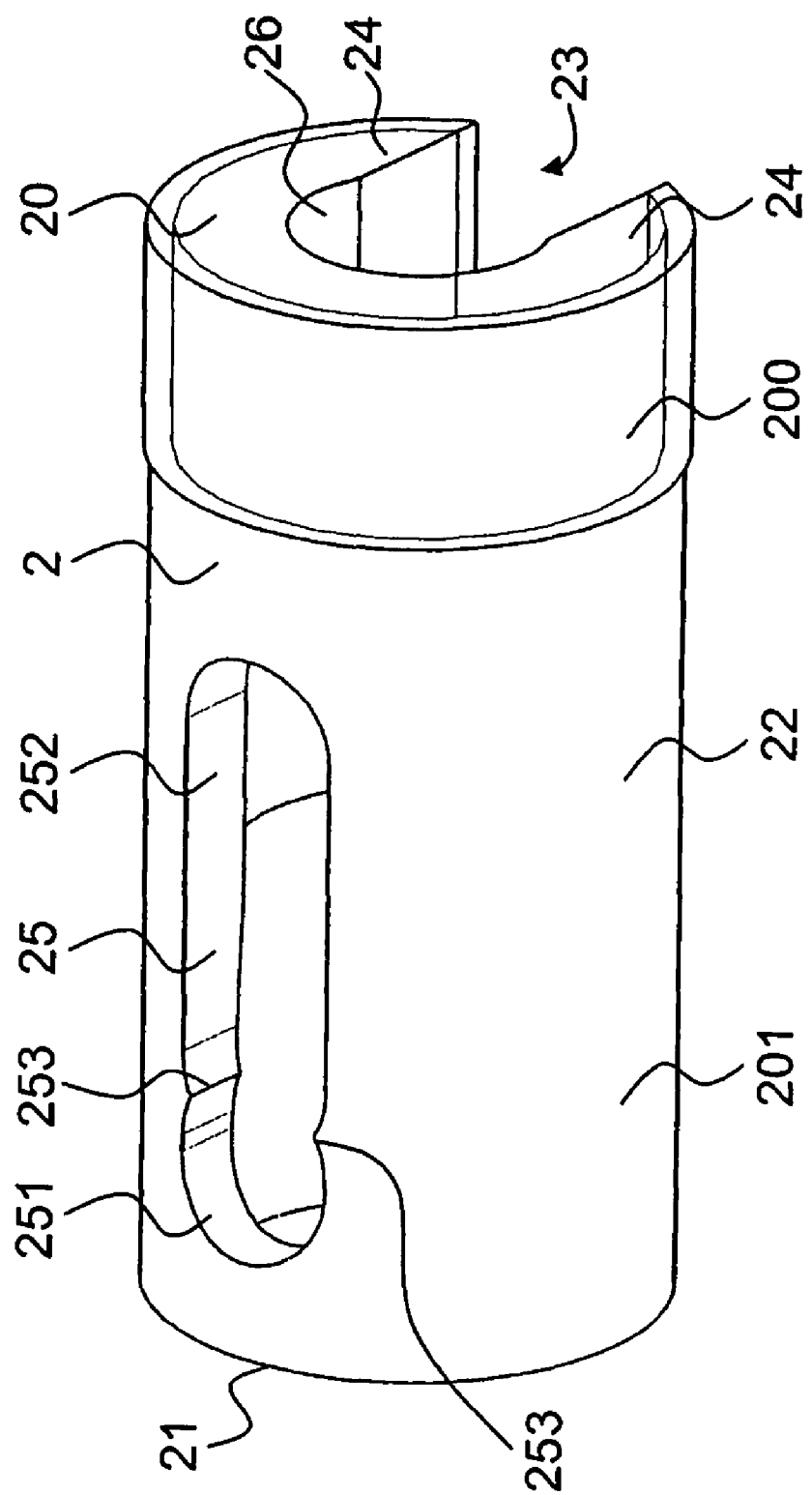
FIG. 8 shows a perspective view of a locking element of a wire fixation device according FIG. 1.

The locking element 2 which is also shown in FIG. 8 has a substantially cylindrical form, wherein said cylinder comprises a first end face 20, a second end face 21 and a circumferential surface 22. In a first section 200, the circumferential surface 22 comprises a larger outer diameter than in an adjacent second section 201. A reception or opening 26 extends through the locking element 2 from the first end face 20 to the second end face 21. Reception 26 forms a part of the through opening 5 for accommodating the wire. The opening or reception 26 comprises several sections 261, 262, 263 which are explained below. Due to the cylindrical form and the reception 26 one can also say that the locking element 2 has the shape of a hollow cylinder with a sidewall 24. A slot 23 extending from the first end face 20 to the second end face 21 and from the circumferential surface 22 into the reception 26 is arranged within the sidewall 24. Said slot 23 interrupts the sidewall 24 over the whole length. The slot 23 can have a width that is slightly larger than the diameter of the wire to be inserted via the slot 23 into reception 26 as will be explained below.

The first section 200 comprises preferably an external thread. The external thread can be used to be in engagement with a tool in order to remove the locking element 2 from an engagement with the clamping cone 3 once the wire has to be removed from the wire post. This means that the locking element 2 will be extracted from the engagement by means of the tool. In other embodiments the first section 200 may have a different shape, such as an angular shape. It is important however, that the medical practitioner may grasp the second portion by means of a tool in order to extract the locking element 2 out of the clamping cone 3.

In the preferred embodiment groove 25 comprises two sections, namely a first section 251 and a second section 252. The two sections are divided by means of a notch 253 that extends into the groove 25. In the initial position the bolt 4 extends into the first section 251. Due to the arrangement of the notch 253 and the extension of the bolt 4 the locking element 2 will be held in its position. As mentioned herein the locking element 2 has to be moved in axial position in order to fix the wire 6. In order to conduct such a movement an axial force has to be provided on to the locking element such that the notch 253 passes the bolt 4 which extends then into the second section 252. The arrangement of the notch 253 prevents the medical practitioner from closing the device accidentally.

The locking element 2 comprises furthermore a groove 25 that is arranged in the sidewall 24 across from the first slot 23. The groove 25 is preferably surrounded by the sidewall 24 and extends from the circumferential surface 22 into the reception 26, i.e. through the sidewall 24 in radial direction.

Figures 7A, 7B:
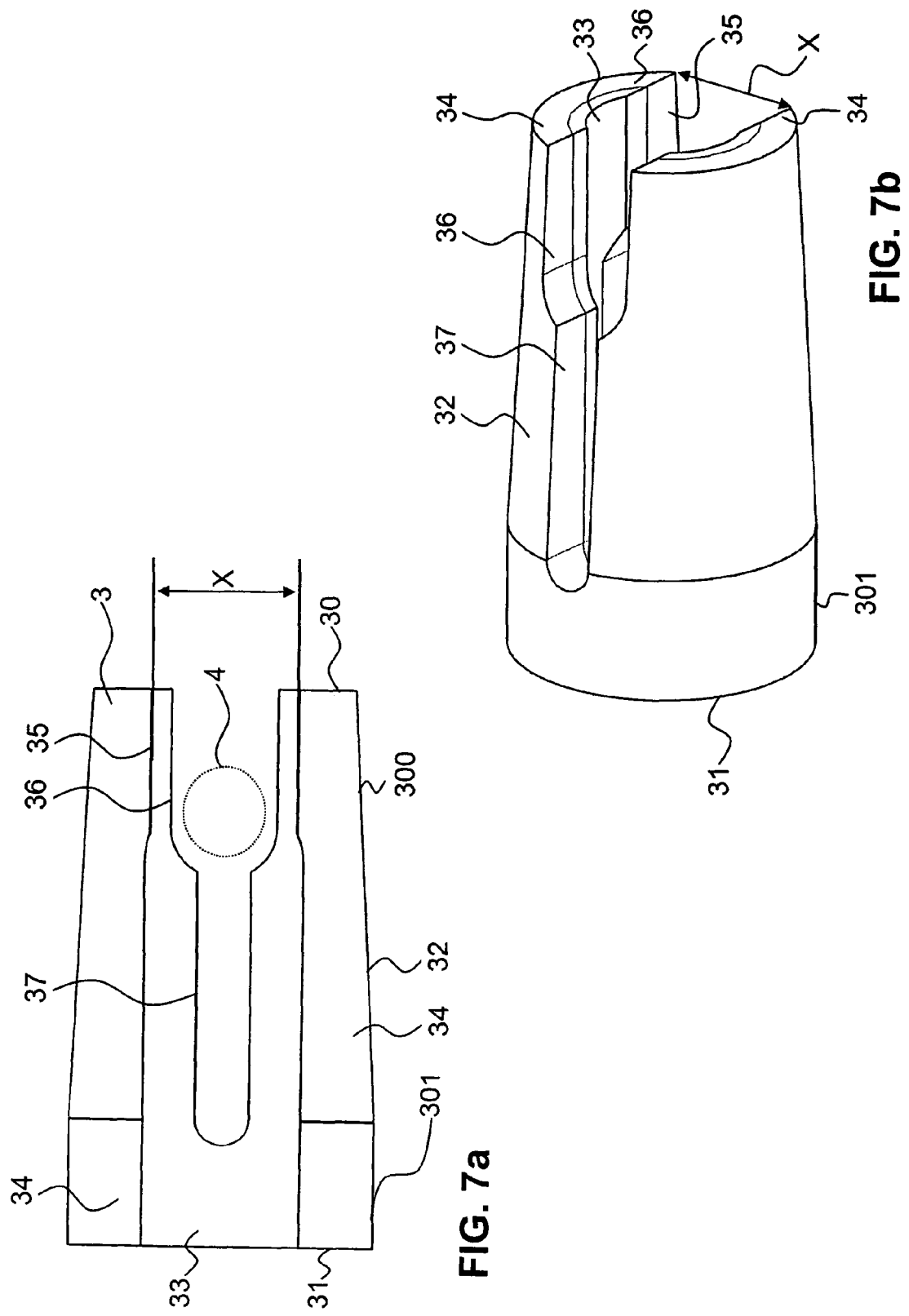
FIGS. 7*a/b* show a bottom view and a section view of the clamping cone of a wire fixation device according FIG. 1.

The clamping cone 3 is also substantially cylindrical comprising a first end face 30, a second end face 31 and a circumferential surface 32. Reference is also made to FIGS. 7a/b. The circumferential surface 32 comprises a first section 300 and a second section 301. The first section 300 is adjacent to the first end face 30. The second section 301 follows the first section 300 and adjoins the second end face 31. The first section 300 comprises an inclined surface in the embodiment shown a conic shape. It is understood that an inclined surface or section is a section whose cross-sectional surface increases along a middle axis. The conicity is arranged such that the diameter increases from the first end face 30 towards the second section 301. Preferably the cone angle is between 2° and 15° preferably between 4° and 8°. The second section 310 comprises a constant diameter over its whole length. As it can be seen from FIG. 1 the length of the first section 300, i.e. the conic section, is larger than the length of the second section 301.

The clamping cone 3 comprises furthermore a clamping opening 33 extending through the clamping cone 3 from the first end face 30 to the second end face 31. Clamping opening 33 forms a part of said through opening 5 and is preferably dimensioned such that it clamps the wire. The surface of said opening comprises preferably a smooth surface in order to provide a force closure with the wire. This means that the wire will be held by a frictional force. Alternatively, the surface of said opening 33 comprises a teethed or a roughened surface. Such a surface has the advantage that the engagement between the wire and the clamping cone 3 will be improved. This is due to the fact that said teeth provide additionally to a form closure as the teeth enter into the surface of the wire. In other embodiments it is also possible that clamping cone 3 is deformed such that the wire will be squeezed by the clamping cone 3 in order to obtain a form closure between the wire and the clamping cone 3. The smaller width and/or the tapered sidewall allows to snap the wire into the clamping cone 3 and to hold it in clamping cone 3. This means that the wire is held in the opening 33 of the clamping cone 3. The clamping cone 3 has the shape of a hollow cylinder having a sidewall 34. Sidewall 34 is interrupted by a slot 35 extending from the first end face 30 to the second end face 31 and from the circumferential surface 32 to the clamping opening 33. As it will be mentioned below in more detail, the slot 35 has a width X that is slightly smaller than the diameter of the wire to be inserted via the slot 35 into clamping opening 33. Over the whole length of the clamping element 3 the width X of the slot 35 may be constant or variable. FIGS. 7a/b show a slot 35 having a smaller width in the first section 300 or in the section close to the first surface 30. Such a variable slot 35 has the advantage that the sidewalls 34 are resilient deformable especially in the region in which the width X of the slot 35 is smaller than the wire diameter. The clamping cone 3 comprises furthermore a groove 36 that is arranged in the sidewall 34 across the slot 35 and an optional groove 37. The groove 36 extends from the first end face 30 partially into the sidewall 34. In the present embodiment the groove 36 extends completely through the sidewall 34 in radial direction. The optional groove 37 extends from groove 36 in axial direction. The groove 37 supports the resilient deformation upon the introduction of a wire. The groove 36 is used to accommodate parts of pin 4. This is shown by means of the broken lines 4. In other embodiments it can also be possible that the groove 36 extends partially from the circumferential surface into the sidewall 34.

The bolt 4 is also substantially cylindrical comprising a first end face 40, a second end face 41 and circumferential surfaces 42, 43, 44 having different diameters.

Reference is now made to FIG. 3 which shows the assembled wire fixation device in a section view. The clamping cone 3 is arranged in the opening 12 of the head portion 11. Thereby the clamping cone 3 is arranged such that the second end face 31 is in contact with the abutment shoulder 14. The locking element 2 is also arranged in the opening 12. In doing so the locking element 2 is arranged such that its reception 26 is contact with the conic or inclined circumferential surface of the first section 300 of the clamping cone 3.

The opening 26 in the locking element 2 comprises a first section 261 being adjacent to the first end face 20, a second section 262 being adjacent to the first section 261 and a third section 263 being adjacent to the second section 262 and the second end face 21. The first section 261 is cylindrical with a constant diameter. The second section 262 is also cylindrical with a constant diameter but the diameter is larger than the one of the first section 261. The third section or inclined or conical section 263 is inclined or conical, respectively and has complementary dimensions in terms of diameter and angle than the inclined or conic section 300 of the clamping cone 3 such that the clamping cone 3 can be in an engagement with the locking element 2.

The locking element 2 is held by means of the bolt 4 within the opening 12. The circumferential surface 43 of bolt 4 is in an engagement with the groove 25 of the locking element 2. Due to the fact that the parts of the bolt 4 protrude into said groove 25, a rotation of the locking element 2 the middle axis 100 is not possible. However, the arrangement permits a longitudinal motion along the middle axis. This motion is limited by the bolt that engages into the locking element 2 as mentioned.

In the present embodiment as shown in FIG. 3, the clamping cone 3 is held in position by means of bolt 4 and an abutment element. The abutment element here is provided by means of abutment shoulder 14. Thereby the clamping cone comprises a groove 35 which is arranged in the sidewall 34. The groove 36 is open towards the first end face 30 and extends to an abutment surface 37. The bolt 4 engages into groove 36 and is in contact with the abutment surface 37 and the clamping cone 3 itself abuts with the second surface 31 on the shoulder 14.

In an other embodiment the groove 36 can have a closed form. Such a groove may also be designated as abutment groove being limited in axial direction by means of two abutment face. The bolt 4 thereby extend into the groove such that it is between the two abutment faces. Upon an axial force on the clamping cone 3 the abutment the bolt abuts on the abutment faces and the axial movement is therefore blocked. This means that the abutment shoulder 14 may be omitted.

Due to that alignment of the locking element 2 and the clamping cone 3 the grooves 23 and 35 of the elements are aligned such that access to the reception 26, clamping opening 33 and opening 12 is provided via said slots. This means that the wire fixation device according to the present invention can be imposed on or slipped over a wire. With other words the wire can be introduced into the opening 26, clamping opening 33 and opening 12 via the slot 13 and the slots 23, 35.

A further advantage of bolt 4 is that the wire post 1, the locking element 2 and the clamping cone 3 form a single unit. This means that the medical practitioner has only one single element to handle.

Once the wire has been placed and connected with the bony structure, the wire fixation device can be imposed on or slipped over the wire such that the wire is arranged in opening 5 or accommodated in clamping opening 33, respectively, and such that the neck portion 11 is arranged within an opening of the medical device. The width of the slot 35 is smaller than the diameter of the wire. The introduction of the wire through the slot 35 into the clamping opening 33 results in slight elastic deformation of sidewalls 34 in radial direction. As soon as the wire is fully inserted in the clamping opening 33 the sidewalls 34 will return into the initial position. The wire is therefore caught in the clamping opening 33. This means that a radial movement with respect to clamping opening 33 is no longer possible but an axial movement with respect to the clamping opening 33 or the opening 5, respectively.

The wire fixation device is oriented such that the end of the wire is arranged near the first section 121 of the opening 12. With reference to FIG. 3 this means that the wire extends from the left to the right, wherein the bony structure is on the right hand side.

As soon as the wire fixation device is arranged in the desired position, the wire can be tensioned by hand and especially by means of a tool. Once the wire has been tensioned it has to be locked or fixed relative to the medical device by means of the wire fixation device.

As the circumferential surface 24 of the locking element 2 is in contact with the second section 122 of the opening 12 of the head portion 10 and as the third part 263 of the reception 26 is in contact with conic first section 300 of the clamping cone 3, the inner diameter of the clamping opening 33 within the clamping cone 3 will be diminished as long as the locking element 2 will be forced into axial direction. Therefore a radial force will be exerted onto the wire that is arranged in opening 5 via the surface of the clamping opening 33 of the clamping cone 3. Said radial force locks the wire relative to the wire post 1 due to a resulting friction force in direction of the wire. This means that the wire is locked relative to the wire fixation device by means of a frictional fit.

It has to be noted that when the wire fixation device is used with an external fixator having the shape of a ring, two wire fixation devices have to be used in order to fix a wire to the ring on two opposite sides. The dimension of a wire usually allows the reception of tensile forces but the wire may also be a pin having dimensions which allow compressive forces as well.

Preferably all the elements as described herein are made out of metal. The wire post 1, the locking element 2, and the bolt 4 are preferably made out of steel or titanium. The clamping cone 3 is preferably made out of hardened steel or hard metal (carbide).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A wire fixation device for fixing a wire or a pin to a medical device comprising
   a wire or a pin,
   a wire post having a head portion with an opening having a predetermined longitudinal axis for reception of said wire and a neck portion for being in engagement with an opening of the medical device,
   a locking element that is introduced into the opening having an opening with inclined sections that are inclined to the longitudinal axis,
   an abutment element, and
   a clamping cone having a clamping opening in which said wire or said pin is arranged and inclined outer surfaces that are inclined to the longitudinal axis,
   wherein said clamping cone abuting on said abutment element and wherein said clamping cone is received at least partly in said opening of said locking element thereby said inclined surfaces of the clamping cone are in engagement with the inclined sections of the locking element such that upon an axial displacement of the locking element relative to the clamping cone a radial force is exerted onto the clamping cone leading to a reduction of the diameter of the clamping opening such that a radial force results onto said wire or said pin which is inserted into the clamping opening wherein the neck portion is elongated and substantially cylindrical and comprises a slot extending through the neck portion from an end face being opposite the head portion to the opening of the head portion and in that the locking element and the clamping cone each comprise a slot extending along axial direction over the whole length of the respective sidewall and along radial direction from the respective circumferential surface into the respective reception or clamping opening and
   wherein the locking element and the clamping cone are arranged such with respect to each other and to the wire post that a through slot is being provided in order to introduce the wire via the slot in the wire post, via the slot in the locking element and via the slot in the clamping cone into the clamping opening in a direction transverse to the longitudinal axis.

2. The wire fixation device according to claim 1, wherein the inclined section and the inclined outer surface are plane surfaces or curved surfaces such that a conical structure results.

3. The wire fixation device according to claim 1, wherein the slot in the clamping cone has a width that is smaller than the diameter of the wire.

4. The wire fixation device according to claim 1, wherein the head portion comprises an opening in which a bolt is introducible, wherein said bolt engages in a groove that is arranged in the locking element such that the locking element will be held fixed in radial direction and moveable in axial direction.

5. The wire fixation device according to claim 1, wherein the abutment element is provided by means of said bolt and an abutment shoulder, wherein the bolt engages into a longitudinal groove that is arranged in the clamping cone and that comprises an abutment surface and is open towards a first end face and wherein the clamping cone abuts on said abutment shoulder the other end face.

6. The wire fixation device according to claim 1, wherein the abutment element is provided by means of said bolt and an abutment groove, wherein the dimension of said abutment groove is limited in a direction along the longitudinal axis by means of an abutment face such that upon an axial force the bolt abuts on said abutment face.

7. The wire fixation device according to claim 1, wherein the neck portion comprises recesses that are arranged towards the slot, wherein a fixation element is introducible into said recesses.

8. The wire fixation device according to claim 1, wherein the opening in the clamping cone comprises a smooth surface for providing a force closure with the wire or a teethed surface for providing a form closure with the wire.

9. A wire fixation device for fixing a wire or a pin to a medical device comprising
  a wire post having a head portion with an opening having a predetermined longitudinal axis for reception of a wire or pin and a neck portion for being in engagement with an opening of the medical device,
  a locking element that is introduced into the wire post head portion opening having an opening with inclined sections that are inclined to the longitudinal axis,
  an abutment element, and
  a clamping cone having a clamping opening in which said wire or said pin is arranged and inclined outer surfaces that are inclined to the longitudinal axis,
  wherein said clamping cone abuts on said abutment element and
  wherein said clamping cone is received in said opening of said locking element thereby said inclined surfaces of the clamping cone are in engagement with the inclined sections of the locking element such that upon an axial displacement of the locking element relative to the clamping cone a radial force is exerted onto the clamping cone leading to a reduction of the diameter of the clamping opening such that a radial force results onto said wire or said pin which is inserted into the clamping cone;
  wherein the neck portion is elongated and substantially cylindrical and comprises a slot extending through the neck portion from an end face being opposite the head portion to the opening of the head portion and in that the locking element and the clamping cone each comprise a slot extending along axial direction over the whole length of the respective sidewall and along radial direction from the respective circumferential surface into the respective reception or clamping opening and wherein the locking element and the clamping cone are arranged such with respect to each other and to the wire post that a through slot is being provided in order to introduce the wire via the slot in the wire post, via the slot in the locking element and via the slot in the clamping cone into the clamping opening.

10. The wire fixation device according to claim 9, wherein the inclined section and the inclined outer surface are plane surfaces or curved surfaces such that a conical structure results.

11. The wire fixation device according to claim 9, wherein the slot in the clamping cone has a width that is smaller than the diameter of the wire.

12. The wire fixation device according to claim 9, wherein the head portion comprises an opening in which a bolt is introducible, wherein said bolt engages in a groove that is arranged in the locking element such that the locking element will be held fixed in radial direction and moveable in axial direction.

13. The wire fixation device according to claim 9, wherein the abutment element is provided by means of said bolt and an abutment shoulder, wherein the bolt engages into a longitudinal groove that is arranged in the clamping cone and that comprises an abutment surface and is open towards a first end face and wherein the clamping cone abuts on said abutment shoulder the other end face.

14. The wire fixation device according to claim 9, wherein the abutment element is provided by means of said bolt and an abutment groove, wherein the dimension of said abutment groove is limited in a direction along the longitudinal axis by means of an abutment face such that upon an axial force the bolt abuts on said abutment face.

15. The wire fixation device according to claim 9, wherein the neck portion comprises recesses that are arranged towards the slot, wherein a fixation element is introducible into said recesses.

16. The wire fixation device according to claim 9, wherein the opening in the clamping cone comprises a smooth surface for providing a force closure with the wire or a teethed surface for providing a form closure with the wire.

17. The wire fixation device as set forth in claim 16 wherein the locking element and clamping cone have aligned grooves extending between their respective outer and inner surfaces and further comprising a screw threadably mounted in the head portion for movement in a direction perpendicular to the first axis into and out of the aligned groove in the locking element and clamping cone to prevent relative rotation therebetween.

18. The wire fixation device as set forth in claim 17 wherein the clamping cone comprises an end surface contacting the abutment surface on the head portion for preventing movement of the clamping cone in the direction of the first axis along the inclined surfaces of the clamping cone and locking element engage.

19. The wire fixation device as set forth in claim 16 further comprising means for moving the clamping cone into the internal opening of the locking element along the first axis such that the inclined outer surface of the clamping cone engages the inclined surface of the locking element.

20. A wire fixation device for fixing a wire or pin to a medical device comprising:
  a wire post having a head portion with an opening extending along a first axis and a neck portion extending from the head portion, the neck portion including a slot extending along a second axis generally perpendicular to the first axis, the slot intersecting the opening in the head portion, the head portion having an abutment surface extending into the opening;
  a locking element mounted in the opening of the head portion, the locking element having an internal opening therethrough with a surface inclined with respect to the first axis, a slot extending from the internal opening of the locking element to an outer surface of the locking element;

a clamping cone having a clamping opening therethrough having an inner surface for receiving a wire or pin mounted within the locking element internal opening, the clamping cone having an outer surface inclined with respect to the first axis for engaging the inclined surfaces of the locking element, the clamping cone having a slot extending between the clamping opening and the outer surface, the slots in the clamping cone and the locking element are alignable with the slot in the neck portion so that the wire or pin may be inserted into the clamping cone clamping opening through the wire post neck portion by movement in a plane containing the first and second axis.

* * * * *